US011484481B2

(12) United States Patent
Maddahi et al.

(10) Patent No.: US 11,484,481 B2
(45) Date of Patent: Nov. 1, 2022

(54) ORAL CARE PRODUCTS AND METHODS

(71) Applicant: Oral Health Innovations, LLC, Beverly Hills, CA (US)

(72) Inventors: Kourosh Maddahi, Beverly Hills, CA (US); Hessam Nowzari, Beverly Hills, CA (US)

(73) Assignee: Oral Health Innovations LLC, Beverly Hills, CA (US)

( * ) Notice: Subject to any disclaimer, the term of this patent is extended or adjusted under 35 U.S.C. 154(b) by 15 days.

(21) Appl. No.: 17/039,937

(22) Filed: Sep. 30, 2020

(65) Prior Publication Data

US 2021/0022972 A1 Jan. 28, 2021

Related U.S. Application Data

(63) Continuation of application No. 16/057,663, filed on Aug. 7, 2018, now Pat. No. 10,813,855, which is a continuation-in-part of application No. 15/850,655, filed on Dec. 21, 2017, now Pat. No. 10,813,877.

(60) Provisional application No. 62/552,650, filed on Aug. 31, 2017, provisional application No. 62/465,536, filed on Mar. 1, 2017, provisional application No. 62/437,100, filed on Dec. 21, 2016.

(51) Int. Cl.
*A61K 8/20* (2006.01)
*A61K 8/25* (2006.01)
*A61K 8/9794* (2017.01)
*A61K 8/46* (2006.01)
*A61K 8/34* (2006.01)
*A61Q 11/00* (2006.01)

(52) U.S. Cl.
CPC ................ *A61K 8/20* (2013.01); *A61K 8/25* (2013.01); *A61K 8/345* (2013.01); *A61K 8/463* (2013.01); *A61K 8/9794* (2017.08); *A61Q 11/00* (2013.01)

(58) Field of Classification Search
CPC .......... A61K 8/20; A61K 8/9794; A61K 8/25; A61K 8/345; A61K 8/463; A61Q 11/00
See application file for complete search history.

(56) References Cited

U.S. PATENT DOCUMENTS 10,813,877 B2 * 10/2020 Maddahi ............... A61K 8/9794
2016/0303035 A1 * 10/2016 Kim ....................... A61Q 11/00

FOREIGN PATENT DOCUMENTS

KR 20130027751 A * 3/2013
KR 101481371 B1 * 1/2015

OTHER PUBLICATIONS

Lumineux Oral Essentials Clean and Fresh Toothpaste (accessed May 2, 2019 from https://oralessentials.com/collections/toothpaste/products/clean-fresh-toothpaste-3-75oz; dated Jun. 6, 2016 (Year: 2016).*
Goel (Bamboo Salt Review, accessed May 1, 2019 from http://www.thebamboosalt.com/ MSBoard_View.aspx?boardid=msc02&uid=43&page=1&pg=0&subboardid=&ThreadGroupID=&cid=&boardcategory=&liststyle=STD, dated Sep. 8, 2013 (Year: 2013).*
KR20130027751 A_cha_machine translation (Year: 2022).*
Pradeep. J. Periodontol., vol. 83, No. 6, Jun. 2012, pp. 797-804) (Year: 2012).*
J.R. Witkoff. "Brushing Immediately After Eating May Harm Your Teeth," Internet posting dated Feb. 26, 2015; accessed May 1, 2019 from https://www.awildsmile.com/blog/brushing-after-meals/ (Year: 2015).*
N.Ajmera, A. Chatterjee, V. Goyal. Aloe vera: It's effect on gingivitis. J. Indian Society of Periodontology, vol. 17(4), Jul.-Aug. 2013, 435-438. (Year: 2013).*

* cited by examiner

*Primary Examiner* — Michael P Cohen
(74) *Attorney, Agent, or Firm* — Louis C. Paul

(57) ABSTRACT

Methods of reducing gingivitis and plaque buildup by administering an oral care product (a dentifrice or a mouthwash) that consists essentially of a sea salt, preferably Dead Sea salt, and xylitol. In mouthwash and dentifrice embodiments, the oral care product contains aloe vera leaf juice.

19 Claims, No Drawings

ORAL CARE PRODUCTS AND METHODS

CROSS-REFERENCE TO RELATED APPLICATIONS

This application is a continuation-in-part of pending U.S. patent application Ser. No. 15/850,655, filed Dec. 21, 2017. U.S. patent application Ser. No. 15/850,655 claims the benefit of the following three provisional patent applications: (i) U.S. Provisional Application No. 62/437,100, filed Dec. 21, 2016; (ii) U.S. Provisional Application No. 62/465,536, filed Mar. 1, 2017; (iii) U.S. Provisional Application No. 62/552,650 filed Aug. 31, 2017.

STATEMENT REGARDING FEDERALLY SPONSORED RESEARCH OR DEVELOPMENT

Not applicable.

FIELD OF INVENTION

The present invention relates to compositions and methods for improving the appearance and health of teeth and gums with oral care products containing naturally-derived ingredients.

BACKGROUND OF INVENTION

The therapeutic and medicinal benefits of Dead Sea salts have been reported in the scientific literature, typically in connection with diseases of the skin and joints. See, e.g., Uriel Katz et al., "Scientific Evidence of the Therapeutic Effects of Dead Sea Treatments: A Systematic Review," *Seminars in Arthritis and Rheumatism*, Vol. 42, No. 2 (October 2012), pp. 186-200, citing Z. Even-Paz, J. Shani, "The dead sea and psoriasis: Historical and geographic background," *Int J Dermatol*, Vo. 28, No. 1 (1989), pp. 1-9 (345 g of mineral per liter (34.5% or 34.5 g/100 mL); Id. citing S. Sukenik et al., "The Dead Sea—a unique resort for patients suffering from joint diseases," *Harefuah*, Vol. 149, No. 3 (2010), pp. (175-179)(180 to 215 g of mineral per liter). Dan Buskila et al., "Balneotherapy for Fibromyalgia at the Dead Sea," *Rheumatol Int, Vol.* 20 (2001), pp. 105-108.

The water of the Dead Sea contains concentrated salts other than NaCl—including, but not limited to, $MgCl_2$, $CaCl_2$, KCl, and $MgBr_2$. Among the separate ions present in the Dead Sea water are chloride (212.4 g/l), magnesium (40.85 g/l), sodium (39.15 g/l), calcium (16.86 g/l), potassium (7.26 g/l), bromide (5.12 g/l), sulfate (0.47 g/l), and bicarbonate (0.22 g/l). See, e.g., I. L. Schamberg, "Treatment of psoriasis at the Dead Sea," Int J Dermatol, Vol. 17, No. 6 (1978), pp. 524-525; Paz and Shani, supra.

European Patent Application EP1074245A2 discloses use of mineral salt, in particular Dead Sea salts, as an active ingredient in a mouthwash to "assist in combatting bacteria and gum irritation and inflammation".

Essential oils have been used for the treatment of a variety of ailments since ancient times. The safety and efficacy of essential oils in dentistry have been reported in numerous clinical studies. See, e.g., Namrata Dagli et al., "Essential oils, their therapeutic properties, and implication in dentistry: A Review" *J Int Soc Prev Community Dent.* Vol. 5, No. 5 (2015), pp. 335-340.

The safety and potential for adverse effects from synthetic ingredients, not only for humans but also the larger ecosystem, have long been of concern. These issues were brought to the forefront by Rachel Carson, in her 1962 book, *Silent Spring*, which focused on the impact of pesticides, in particular DDT, on birds. A decade later, in 1973, the United States banned DDT. In that same year, manufacturers and producers of health foods and products began organic certification. Two years later, in 1975, Tom's of Maine introduced what it claimed to be the first mass-marketed "natural" toothpaste. The ensuing decades saw an explosive growth in demand for natural and organic products. By 1990, the organic industry had estimated sales of more than $1 billion. In 2006, Tom's of Maine was acquired by the Colgate-Palmolive Company. In 2015, Whole Foods had expanded to 365 stores and reported record revenues of almost $15.5 billion.

While natural personal care products have gained "mainstream" consumer acceptance, concerns remain. Many so-called "natural" products are not "natural", and contain significant amounts of synthetic ingredients. Other products include "natural" ingredients at de minimis concentrations that do not provide health benefits; instead, natural ingredients are added to these products for purposes of "label copy".

As access to the internet became more widespread, consumers took steps to publicly question what is natural, posting blogs and comments calling attention to what can be viewed as deceptive or misleading use of the word "natural." Additionally, the internet has made do-it-yourself personal product recipes (for skincare, haircare, and oral care) available to consumers. See, e.g., http://www.healthyandnatural-word.com/sage-and-sea-salt-homemade-toothpowder/(¼ cup fresh sage leaves combined with ¾ cup sea salt); see also, http:/www.sproutinghealthyhabits.com/homemade-natural-toothpaste/(2 teaspoons of Dead Sea salt; 3 teaspoons of Himalayan pink salt; 2 teaspoons of ground sage; ⅓ cup of stevia powder; 7-8 tablespoons organic unrefined cold pressed coconut oil; 8 drops of tea tree essential oil; 40 drops spear[mint] essential oil; 15 drops of pepper[mint] essential oil; 5 teaspoons of sodium bentonite clay).

Access to a plethora of information on the internet is not, however, without risk. Website content is not subject to review and can be incomplete, inaccurate, or alarmist. Statements that a particular ingredient is "toxic" are often made without proper context. For example, a 1990 report issued by the US National Toxicology Program found "equivocal" evidence that fluoridated drinking water can cause osteosarcoma in male rats. However, exposure to fluoride has been associated with dental and skeletal fluorosis.

The present invention seeks to meet the long-felt but as yet unmet need for natural and naturally derived oral care products (in particular, dentifrices and mouthwashes) that contain safe and effective amounts of natural ingredients useful in cleaning and maintaining healthy, attractive teeth and gums. Products of the present invention are tailored to address fresher/cleaner breath.

Periodontal disease affects not only oral health. Recent research has identified potential linkage with systemic conditions such as cardiovascular disease, diabetes, adverse pregnancy outcomes, rheumatic arthritis, aspiration pneumonia and Chronic Obstructive Pulmonary Disease. Periodontal disease is also being investigated as a potential etiological factor in colorectal cancer, oral squamous cell carcinoma, pancreatic cancer and breast cancer.

Mechanical plaque control has limited effectiveness in ensuring oral health; it is arduous, repetitive and time-consuming. For this reason, there exists considerable interest in alternative or adjunct approaches to existing mechanical oral hygiene techniques—notably mouthwashes. However, studies report widely varying levels of effectiveness of prior art mouthwashes with regard to plaque removal, and reported side-effects include altered taste and discoloration. Prior art mouthwashes that contain chlorhexidine provide excellent short-term plaque control and concomitant improvement in gingival health. However, use of chlorhexidine mouthwashes is limited due to some of its side effects that include tooth staining and taste alterations after prolonged periods of use. Moreover, chlorhexidine has been shown ex vivo to have a cytotoxic effect on cells. Thus, there is a continued need for new mouthwash formulations for improving plaque control. That need is met by the present invention.

SUMMARY OF THE INVENTION

The present invention is directed to oral care products—toothpastes, mouthwashes, and dental floss—consisting essentially of (i) a sea salt, preferably, Dead Sea salt and (ii) xylitol, and uses of such products to reduce plaque and gingival inflammation. Mouthwash and dentifrice embodiments of the invention also contain aloe vera leaf juice.

DETAILED DESCRIPTION OF THE INVENTION

A basic and novel characteristic of the oral care products of the present invention is the absence of: artificial colors, dyes or flavors; paraben or formaldehyde preservatives; bleaching agents (i.e., peroxides); sodium lauryl sulfate or sodium laureth sulfate; petroleum-derived glycerin; and genetically modified organisms (GMOs).

Another basic and novel characteristic of the oral care products of the present invention is non-cytotoxicity within the framework of ISO 10993-5 "Biological Evaluation of Medical Devices—Tests For In Vitro Cytotoxicity," described in greater detail below. In mouthwash embodiments, a further basic and novel characteristic of the oral care products of the present invention is the absence of ethyl alcohol and/or glycerin; preferably neither ethyl alcohol nor glycerin is present in the mouthwashes of the invention. Certain mouthwash embodiments of the present invention may sometimes be described as "alcohol free." In labeling personal care and cosmetic products, the term "alcohol," used by itself, is to be understood by the person having ordinary skill in the art as referring to ethyl alcohol. Accordingly, products labeled as "alcohol free" may contain other alcohols, including menthol or glycerol.

Collectively, ingredients listed above as absent from the oral care products of the present invention are referred to as "Excluded Ingredients."

In certain preferred dentifrice embodiments, a further basic and novel characteristic of the oral care products of the present invention is the absence of fluoride and/or baking soda; preferably neither fluoride nor baking soda is present in the dentifrices of the invention. In those embodiments, fluoride and/or baking soda are to be considered as Excluded Ingredients. While dentifrice oral care products of the present invention are preferably not fluoridated, fluoride may be included in certain formulations within the scope of the invention to strengthen tooth enamel and remineralize teeth.

Accordingly, in describing and claiming oral compositions as "consisting essentially of a sea salt, preferably Dead Sea salt, at least one essential oil selected from peppermint oil, wintergreen oil, and spearmint oil, xylitol, and preferably, aloe vera leaf juice" it is meant that: (a) each of the following two ingredients are essential and, therefore, required component ingredients of the oral care products of the present invention: (i) sea salt, preferably Dead Sea salt, and (ii) xylitol are essential and required component ingredients that are present in the oral care products; and (b) Excluded Ingredients are not present in the oral care products. Mouthwash and toothpaste embodiments contain aloe vera leaf juice as an essential and required component ingredient.

Preferably, as a further required and essential ingredient, the oral care products of the present invention contain at least one essential oil selected from peppermint oil, spearmint oil, and wintergreen oil. Even more preferably, the at least one essential oil is spearmint oil.

As used in the present application, an "essential oil" is a mixture of terpenic hydrocarbons, especially monoterpenes and sesquiterpenes, and oxygenated derivatives such as aldehydes, ketones, epoxides, alcohols, and esters.

"Non-cytotoxicity" of oral care products of the present invention is confirmed within the framework of ISO 10993-5:2009 based on the widely-used Trypan blue exclusion test. (Trypan blue is a colorant which stains dead cells, i.e., cells with loss of membrane integrity.) More particularly, Balb/c 3T3 clone A31 cells (ATCC CCL 163; 86th passage) are seeded in multi-well plates (24 wells, each 15.5 mm in diameter) at the starting density of 30,000 cells/cm$^2$ in culture medium—Dulbecco's Modified Eagle Medium (DMEM)—supplemented with 10% (v/v) fetal calf serum (FCS). No antibiotics are used. Cultures are incubated at 37° C. in a humidified atmosphere containing 5% (v/v) $CO_2$, for 24 hours, and are examined with a microscope to verify a sub-confluent monolayer with less than de minimus alteration in morphology. Culture medium is withdrawn and replaced with a solution of one of the following: oral care products of the present invention at 5,000 µg/mL, as well as dilutions 1,500 µg/mL, 500 µg/mL and 150 µg/mL; a "negative" control (phenol, Chemical Abstract Service No. 108-95-2, 0.64 mg/mL); and a "positive" control (DMEM supplemented with 10% (v/v) FCS and 1% antibiotics (v/v). A positive control is defined as statistically significant (30% or greater) inhibition of cell growth as compared to the negative control.

Wells are incubated at 37° C. in a humidified atmosphere containing 5% (v/v) $CO_2$, for a 24-hour period. Photomicrographs are taken (320× magnification) showing the cell layer in contact with the negative control, the positive control and the oral care product of the present invention. Morphology and cell density of the cultures are observed. At the end of the incubation period, culture medium is removed. Cells are detached for two minutes using 250 µL trypsin (0.05% (w/v) in Hank's balanced solution Ca++ and Mg++ free supplemented with 1 mM EDTA. 250 µL of a Trypan blue solution at 0.2% (w/v) in 0.15 M NaCl and 10% (v/v) FCS are added. Cells are incubated for two minutes. Living cells (uncolored) are counted using a hemocytometer. Cell morphology and cell density of medium treated with 5,000 µg/mL of the oral care product of the present invention are observed to be comparable to those of negative control; neither shows statistically significant (30% or greater) inhibition of cell growth. In contrast, cells treated with the positive control show greater than 50% inhibition on cell growth.

"Dental floss" is a cord of thin filaments used to remove food and plaque from between teeth. "Flossing" means the mechanical cleansing of proximal tooth surfaces with dental floss, subgingivally and supragingivally.

Numbers used in describing quantities of ingredients and/or reaction conditions are to be understood as being modified in all instances by the term "about."

Unless otherwise indicated, percentages, parts and ratios are to be understood as based upon the total weight of the composition.

Numerical ranges are meant to include numbers within the recited range, and combinations of subranges between, the given ranges. For example, a range from 1-5, includes 1, 2, 3, 4 and 5, as well as subranges such as 2-5, 3-5, 2-3, 2-4, 1-4, etc.

"At least one" means one or more, and also includes individual components as well as mixtures/combinations.

By the term "dentifrice" is meant a preparation for cleansing and polishing the teeth, that may, and preferably does provide one or more therapeutic benefits (as described below). As will be understood by the skilled artisan, a dentifrice (also referred to in the art and in this application as a "toothpaste") may be formulated as a paste, gel or powder and is preferably applied with a toothbrush.

Dentifrice embodiments of the present invention are administered by brushing the teeth for at least 30 seconds, preferably for at least 60 seconds, most preferably for at least 120 seconds, at least once per day, in the evening prior to going to sleep, preferably with no eating or drinking within 30 minutes after administration.

By "brushing" is meant placing the bristles of a toothbrush in contact with the teeth, preferably at an angle of about 45 degrees to the gum line (where the gums and teeth meet), and moving the bristles in gentle, short strokes along the outer surfaces (cheek side), the inside surfaces (tongue side) and the chewing surfaces of all teeth. The strokes may be in a back-and-forth motion (side-to-side, or up-and-down) or a circular motion. After brushing, the dentifrice is expectorated.

Still more preferably, dentifrice embodiments of the present invention are administered by brushing the teeth for at least 30 seconds, preferably for at least 60 seconds, most preferably for at least 120 seconds, twice daily—once in the evening prior to going to sleep; and once in the morning after breakfast, preferably with no eating or drinking within 30 minutes after administration.

In each administration, about 0.25 grams of the dentifrice of the present invention, preferably at least about 0.5 grams is dispensed on to the bristles of a toothbrush and brushed onto the teeth. In certain preferred embodiments, the dose of toothpaste per administration ranges from about 0.4 to about 0.6 grams.

By the term "mouthwash" is meant a solution that is swished, preferably vigorously, around the mouth, and then expectorated, thereby cleaning the mouth and making the breath smell pleasant.

Mouthwash embodiments of the present invention are administered by swishing about 15-20 ml (about 0.5-0.75 fluid ounces) in the mouth, for a period of time sufficient to contact the teeth, the gums, the roof of the mouth and the tongue. Preferably, mouthwash is swished for at least 30 seconds, more preferably for at least 60 seconds, at least once per day, in the evening prior to going to sleep.

Still more preferably, mouthwash embodiments of the present invention are administered for at least 30 seconds, preferably for at least 60 seconds, twice daily—once in the evening, after brushing prior to going to sleep; and once in the morning after brushing after breakfast.

In especially preferred embodiments, a person practicing an oral care regimen in accordance with present invention (e.g., a consumer or a patient) brushes his/her teeth with a dentifrice of the invention for at least 30 seconds, more preferably for at least 60 seconds, and then swishes a mouthwash of the invention in his/her mouth for a period of at least 30 seconds, preferably at least 60 seconds—a period of time sufficient for the mouthwash to contact the teeth, the gums, the roof of the mouth and the tongue.

Persons practicing methods of the present invention are instructed to abstain from drinking or eating for at least 30 minutes after administering the oral care products of the invention; and, since oral care products of the invention are not intended for ingestion, to expectorate the oral care product after use (i.e., brushing in the case of a dentifrice, or swishing in the case of a mouthwash).

Sea salt is a mixture of inorganic salts from sea water or from inland bodies of salt water. Sea salt may be in the form of a precipitate (on the bottom of a marsh or salt pan or flat) or crystals that float on the surface of the water (known as fleur de sel).

One particularly preferred sea salt suitable for use in the oral care products of the present invention is Dead Sea salt, which is a mixture of natural hygroscopic minerals and micronutrients found in the Dead Sea and is comprised of sodium chloride, magnesium, potassium, and calcium chlorides and bromides. A non-limiting compositional analysis of Dead Sea salt versus common salt is presented in the table below:

| | Dead Sea Salt (%) | Common Salt (%) |
|---|---|---|
| $H_2O$ | 37.5 | 0.33 |
| $MgCl_2$ | 32.2 | 0.18 |
| KCl | 24.5 | 0.14 |
| NaCl | 5.6 | 99.2 |
| $CaCl_2$ | 6.23 | 0.15 |
| $Br^-$ | 0.35 | 0.052 |
| $Rb^+$ | 0.025 | — |
| $Li^+$ | 1.0 | — |
| $Fe^{3+}$ | 0.00203 | 0.00016 |
| $Al^{3+}$ | 0.00037 | 0.000028 |
| $SO_4^{2-}$ | 0.00916 | 0.0311 |
| $Sr^{2+}$ | 0.00153 | 0.00047 |
| $Mn^{2+}$ | 0.00023 | 0.0038 |

S. Halevy et al., J. Eur. Acad. Dermatol. Venereol., Vol. 9, pp. 237-242 (1997).

Another preferred sea salt suitable for use in the oral care products of the present invention is Himalayan salt, which is harvested from the Punjab Region of Pakistan, and is comprised of sodium chloride (about 95-98%), with about 2 to 3% polyhalite (potassium, calcium, magnesium, sulfur, oxygen, hydrogen), fluoride, iodine, and smaller amounts of other trace minerals.

Dead Sea salt is present in oral care products of the invention of the invention at a concentration of less than about 3%, preferably a concentration of from about 0.1% to 2%, still more preferably a concentration of from about 0.5% to about 1.5%.

Xylitol is a pentahydric alcohol and is present in oral care products of the invention at a concentration of at least about 7.5%, more preferably at least about 10%, or at a dose of about 0.1 g/brushing or rinsing.

Aloe vera leaf juice useful in mouthwash and toothpaste embodiments of the present invention preferably contains (i) glycosides at a concentration of at least about 1%, preferably at least about 2%, and still more preferably at about 3%, as well as (ii) at least two, preferably three, anti-inflammatory agents selected from the group of anthraquinones, sterols, auxins and gibberellins and (iii) and immunomodulatory muccopolysachharides, preferably Acemannan.

Oral care products of the present invention contain one or more essential oils selected from the group consisting of spearmint oil, wintergreen oil, and peppermint oil.

Spearmint oil is the volatile oil obtained from the leaves of *Mentha viridis* (also known as *Mentha spicata*).

Wintergreen oil is the volatile oil obtained from the leaves of *Gaultheria procumbens*.

Peppermint oil is a volatile oil obtained from the whole plant *Mentha piperita*.

In one set of preferred embodiments, oral care products of the present invention include at least one essential oil in the genus *Mentha*, selected from *Mentha piperita* (peppermint) oil and *Mentha viridis* (spearmint) leaf oil.

In yet another preferred embodiment, oral care products of the present invention include *Gaultheria procumbens* (wintergreen) leaf oil.

In one even more preferred embodiment, oral care products of the present invention include peppermint oil and one of wintergreen oil or spearmint oil.

In another even more preferred embodiment, oral care products of the present invention include wintergreen oil and one of peppermint oil or spearmint oil.

In a still further even more preferred embodiment, oral care products of the present invention include spearmint oil and one of peppermint oil or wintergreen oil.

In especially preferred embodiments, the oral care products of the present invention contain spearmint oil, peppermint oil, and wintergreen oil.

Menthol, an alcohol that can be Isolated from peppermint or other mint oils, can also be used in oral care products of the present invention.

Oral care products of the present invention also preferably include oils of one or both of *Ocimum basilicum* (basil) or *Eugenia caryophyllus* (clove flower).

In certain preferred embodiments of the invention, basil oil is present at a concentration of up to about 0.5%.

In certain preferred embodiments of the invention, clove oil is present at a concentration of at least about 0.005%. In other preferred embodiments of the invention, dove oil is present at a concentration of at least about 0.01%. In certain of these preferred embodiments, clove oil is preferably at a concentration of up to about 0.02%.

Other essential oils that may be included in oral care products of the present invention include *Melaleuce altemifolia* (tea tree) leaf oil, the oil distilled from the leaves of the *Melaleuca altemifolia*, and *Zingiber officinale* (ginger) root oil, which is obtained from the dried rhizomes of *Zingiber officinale*.

Dentifrice embodiments of the present invention may include mild abrasives (to remove debris and residual surface stains), humectants (to prevent water loss in the toothpaste), thickening products, also known in the art as binders (to stabilize the toothpaste formula), flavoring products (for taste) and detergents (to create foaming action).

Mild abrasives suitable for use in the toothpaste embodiments of the present invention include calcium carbonate, dehydrated silica gels, hydrated aluminum oxides, magnesium carbonate, phosphate salts and slicates. Silica, also called silicone dioxide, bentonite day and hydrated silica are minerals. Some toothpastes of the present invention preferably contain hydrated silica.

Humectants that may be, and preferably are, ingredients in toothpastes of the present invention include glycerin, preferably vegetable glycerine, propylene glycol, and sorbitol.

Glycerin, a sugar alcohol that can be synthesized or obtained from natural sources, is an especially preferred humectant used in toothpastes of the invention.

Non-limiting examples of thickening products that may be, and preferably are included in toothpaste embodiments of the present invention include gums and colloids. Preferred colloids are of marine origin, even more preferably seaweeds.

Two preferred gums are xanthan gum and biosaccharide gum-1; both are polysaccharides derived from the fermentation of carbohydrates. Xanthan gum is derived from glucose or corn syrup. Biosaccharide gum-1 is derived from sorbitol.

Carrageenan, a polysaccharide hydrocolloid obtained from edible red seaweeds in the Gigartinaceae or Solieriaceae families, may be, and preferably is, present in toothpastes of the invention.

Methods of the present invention reduce the amount of plaque by at least 10%, preferably at least 20%, more preferably by at least 30%. Plaque levels can be measured, for example, by the Quigley-Hein Plaque Index (defined by G. A. Quigley and J. W. Hein in 1962 and modified by S. Turesky, N. D. Gilmore, and I. Glickman in 1970), a system for scoring the amount of plaque buildup on teeth that is well-known to the person having ordinary skill in the art (PHOSITA) of dentistry.

More particularly, the PHOSITA scores the amount of plaque on each facial or lingual surface of each tooth that is examined. t third molars. Scores ranging from 0 to 5 are assigned as follows: 0—no plaque; 1—separate flecks of plaque at the cervical margin of the tooth; 2—a thin continuous band of plaque (up to one mm) at the cervical margin of the tooth: 3—a band of plaque wider than one mm but covering less than one-third of the crown of the tooth; 4—plaque covering at least one-third but less than two-thirds of the crown of the tooth; 5—plaque covering two-thirds or more of the crown of the tooth. The Quigley-Hein Plaque Index does not take evaluate third molars and does not take into account plaque buildup on dental restorations (i.e., bridges, crowns, veneers, inlays, and onlays made of porcelain or composite resin). The overall Quigley-Hein Plaque Index (for the entire mouth) is determined by dividing the total score by the number of surfaces examined.

Methods of the present invention reduce gingival inflammation based on the Löe-Silness gingival index preferably at least 25%, more preferably by at least 50%, even more preferably by at least 75%. The Löe-Silness gingival index is a system for scoring gingival inflammation that is well-known to the PHOSITA of dentistry. A score ranging from 0-3 is assigned, where 0.1-1.0 is indicative mild inflammation; 1.1-2.0 indicates moderate inflammation; and 2.1-3.0 indicates severe inflammation. Overall GI is obtained by adding the values of each tooth and dividing by the number of teeth examined.

Reduction in gingival inflammation can also be expressed in terms of the redness coordinate In the CIE 1976 ($L^*a^*b^*$) system, in which "$L^*$" value represents comparative lightness/darkness (lower $L^*$ being indicative of darker), and "$a^*$" and "$b^*$" values represent chromaticity coordinates (red-green and blue-yellow, respectively). See A. R. Robertson, "The CIE 1976 color-difference formulae," *Color Res. Appl.* Vol. 2, pp. 7-11 (1977). Each of the $L^*$, $a^*$ and $b^*$ can be plotted in three-dimensional space to characterize a color in absolute terms. The magnitude of the difference between two colors, as perceived by the human eye, is proportional to the distance between two points defining the two colors on the three-dimensional plot. The difference between the two colors, the Euclidean distance (ΔE), is defined by the following equation: $\Delta E^{*}ab=[(\Delta L^{*})^{2}+(\Delta a^{*})^{2}+(\Delta b^{*})2]^{1/2}$.

Methods of the present invention may also be practiced by flossing with a dental floss comprised of filaments that are coated with a sea salt, preferably Dead Sea salt, and xylitol. Preferably, the filaments are coated with spearmint.

EXAMPLES

The following examples illustrate compositions and methods of practicing of the present invention in some of its embodiments; the examples should not be construed as limiting the scope of the invention. Other embodiments will be apparent to one skilled in the art from consideration of the specification and examples. It is intended that the specification, including the examples, is considered exemplary only without limiting the scope and spirit of the invention.

Some of the examples illustrate preferred embodiments of the invention. Variations of these preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, unless otherwise indicated herein or otherwise clearly contradicted by context, the inventions include all modifications and equivalents of the subject matter disclosed and recited in the claims appended hereto as permitted by applicable law.

Dentifrice Examples

Dentifrices of the present invention are formulated for use by the general population—persons not having sensitivity or xerostomia—and contain the following ingredients at the following concentrations:

Dead Sea salt is present in toothpastes of the invention at a concentration of less than about 3%, preferably from about 0.5% to 2%, most preferably from about 0.75% to about 1.5%.

Xylitol is present in toothpastes of the present invention at a concentration of at least 10% or at a dose of 0.1 g/brushing.

Aloe vera leaf juice is present in toothpastes formulated for use by the general population at a concentration of at least about 10%, preferably at least about 20%, and most preferably at least about 40%.

*Mentha piperita* (peppermint) oil is present in toothpastes of the invention at a concentration of less than 1%, preferably less than about 0.075%, more preferably at a concentration of less than about 0.05%, and even more preferably at a concentration of about 0.03%.

*Mentha viridis* (spearmint) oil is present in toothpastes of the invention, preferably at a concentration of up to about 4%, preferably up to about 2%, more preferably up to about 1%, and still more preferably less than about 0.5%.

*Gaultheria procumbens* (wintergreen) leaf oil is present in toothpastes of the invention, preferably at a concentration of up to about 1%, preferably from about 0.25% to about 0.5%.

In some preferred toothpaste embodiments, the weight ratio of wintergreen oil to peppermint oil is about 10:1.

In other preferred toothpaste embodiments, the weight ratio of spearmint oil to peppermint oil is about 3:1.

In still other preferred toothpaste embodiments, the weight ratio of wintergreen oil to spearmint oil is about 3:1.

In one preferred mouthwash embodiment, the weight ratio of wintergreen to peppermint is from about 6:1 to about 5:1.

In another preferred mouthwash embodiment, the weight ratio of spearmint to peppermint is about 5:3.

In still another preferred mouthwash embodiment, the weight ratio of wintergreen to spearmint is about 4:1.

Basil oil (also known as *Ocimum tenufiorum* oil) is present in toothpastes of the invention, preferably at a concentration of up to about 0.05%.

Clove oil is present in toothpastes of the invention, preferably at a concentration of up to about 0.05%.

Glycerin is present in toothpastes formulated for use by the general population at a concentration of from about 2.5% to about 20%, preferably from about 5.0% to about 15%.

Carrageenan may be, and preferably is, present in toothpastes of the invention, preferably at a concentration of at least about 0.05%. preferably about 0.1%. Even more preferably, carrageenan is food-grade.

Xanthan gum may be, and preferably is present in toothpastes of the invention, preferably at a concentration of at least about 0.10.

Titanium dioxide may be present in certain toothpastes of the invention; when present, titanium dioxide is present at a concentration of up to about 0.6%.

Hydrated silica may be, and preferably is, present in toothpastes of the invention, at a concentration of from about 10% to about 25%.

Toothpastes of the present invention contain a foaming anionic other than sodium lauryl sulfate, preferably sodium methyl cocoyl taurate or sodium lauroyl sarcosinate. In certain preferred embodiments, sodium methyl cocoyl taurate is present in toothpastes of the invention at a concentration of up to about 2%.

Mouthwash Examples

Dead Sea salt is present in mouthwashes formulated for use by the general population at a concentration of from about 0.5% to about 5%, preferably from about 0.75% to about 3%, and most preferably from about 1% to about 2%.

Xylitol is present in mouthwashes formulated for use by the general population at a concentration of from about 5% to about 30%, preferably from about 7% to about 15%, and most preferably from about 8% to about 12%.

Aloe vera leaf juice is present in mouthwashes formulated for use by the general population at a concentration of from about 10% to about 90%, preferably from about 20% to about 85%, and most preferably from about 50% to about 70%.

Clove flower oil is present in mouthwashes formulated for use by the general population at a concentration of from about 0.005% to about 0.075%, preferably from about 0.01% to about 0.04%, and most preferably from about 0.01% to about 0.03%.

Basil oil is preferably present in mouthwashes formulated for use by the general population at a concentration of from about 0.005% to about 0.5%, preferably from about 0.01% to about 0.2%, and most preferably from about 0.02% to about 0.1%.

Peppermint oil is present in mouthwashes formulated for use by the general population at a concentration of from about 0.005% to about 0.12%, preferably from about 0.01% to about 0.1%, and most preferably from about 0.02% to about 0.09%.

Spearmint oil is present in mouthwashes formulated for use by the general population at a concentration of from about 0.01% to about 1%, preferably from about 0.02% to about 0.17%, and most preferably from about 0.05% to about 0.15%.

Wintergreen oil is present in mouthwashes formulated for use by the general population at a concentration of from about 0.03% to about 1%, preferably from about 0.05% to about 0.5%, and most preferably from about 0.1% to about 0.45%.

Clinical Testing Example: Reduction in Plaque Presence and Gingival Health

Ten test subjects were recruited to participate in a double-blinded clinical study. Over a period of twenty days, participants followed three different oral care regimens—each a "study arm" lasting three days: (i) administering a mouthwash of the present invention, (ii) administering a control mouthwash, and (iii) not administering any mouthwash.

Three days prior to the beginning the first study arm, subjects abstained from oral hygiene—no teeth brushing, no use of mouthwash, no chewing gum. For the duration of each study arm, subjects abstained from brushing the lower anterior teeth.

Three clinical endpoints were recorded before and after each of three study arms: (i) plaque index ("PI"), based on the Turesky Modification of Quigley-Hein Index; (ii) gingival inflammation ("GI") based on the Löe-Silness gingival index; and (iii) sulcus bleeding ("mSBI").

Each study arm was followed twice daily—before going to sleep and in the morning after eating breakfast. In study arms (i) and (ii) participants vigorously swished with the assigned mouthwash for at least one minute.

Between the first and second study arm, and again between the second and third study arm, participants entered a one-week wash out period, during which time they brushed with CREST® PRO-HEALTH™ toothpaste (Procter and Gamble, Cincinnati, Ohio) using a new ORAL B® PRO-FLEX™ toothbrush (Procter and Gamble, Cincinnati, Ohio) for each washout period of the study. Use of other oral hygiene measures was not permitted, including chewing gum. Additionally, in order to minimize potential crossover effects, the sequence of mouthwash usage was randomized so that 3 subjects used the mouthwash of the invention as the first study arm; 3 subjects used the control mouthwash as the first study arm; and 4 subjects used no mouthwash at all as the first study arm.

Plaque was scored on a scale of 0 to 5 according to the Turesky modification of the Quigley-Hein Plaque Index. Gingival health was evaluated using the Löe-Silness gingival index and the Sulcus Bleeding Index.

Using a 2-sided T-test and standard statistical approaches for crossover studies, the endpoint and baseline values for each parameter were compared. None of the data showed any evidence of a significant carryover effect (i.e., from one study arm to the next arm). For all of the clinical indices measured, the mouthwash of the invention effects did not differ significantly from those of the control mouthwash ($p>0.164$). Both mouthwashes removed plaque and maintained gingival health more effectively than when no mouthwash was used ($p<0.05$).

More particularly, three days of using the mouthwash of the invention or the control mouthwash reduced plaque presence and gingival inflammation to a very similar degree. Plaque indices were reduced by approximately 30% after 3-day use of either mouthwash, whereas plaque levels increased by approx. 25% when no mouthwash was used. Gingival indices and plaque buildup were significantly reduced after use of either mouthwash, whereas they increased significantly in the absence of a mouthwash regimen.

The invention claimed is:

1. A method for reducing gingival inflammation by at least 25% as measured on the Löe-Silness gingival index comprising a step of daily administration for at least 60 seconds of a mouthwash consisting essentially of
    (a) Dead Sea salt at a concentration of from about 0.5% to about 3.0%,
    (b) Aloe vera leaf juice at a concentration of at least 50% wherein the mouthwash does not contain a bleaching agent and does not contain a fluoride source.

2. The method of claim 1 wherein the daily administration step is performed twice daily, each time for 30 seconds.

3. The method of claim 2 wherein the daily administration step is performed (i) a first time in the evening, prior to going to sleep, and (ii) a second time in the morning, after breakfast.

4. The method of claim 1 wherein the daily administration step is performed once daily for 60 seconds.

5. The method of claim 4 wherein the daily administration step is performed twice daily, each time for 60 seconds.

6. The method of claim 1 wherein the mouthwash further consists essentially of xylitol at a concentration of at least 5%.

7. The method of claim 6 wherein the mouthwash further consists essentially of at least one mint oil selected from the group consisting of wintergreen oil and spearmint oil.

8. The method of claim 7 wherein the at least one mint oil is wintergreen oil at a concentration of from 0.1% to 0.5%.

9. The method of claim 7 wherein the mint oil is spearmint oil at a concentration of up to 1.0%.

10. The method of claim 1 wherein the mouthwash further consists essentially of at least one an anti-inflammatory oil selected from the group consisting of holy basil oil (*Ocimum tenuiflorum*) and clove oil.

11. The method of claim 10 wherein the at least one anti-inflammatory oil is holy basil oil (*Ocimum tenuiflorum*) at a concentration of up to 0.5%.

12. The method of claim 10 wherein the at least one anti-inflammatory oil is clove oil at a concentration of at least 0.01%.

13. The method of claim 1 wherein the mouthwash further consists essentially of xylitol at a concentration of at least 5% and at least one mint oil selected from the group consisting of wintergreen oil and spearmint oil.

14. The method of claim 1 wherein the mouthwash further consists essentially of xylitol at a concentration of at least 5% and at least one anti-inflammatory oil selected from the group consisting of holy basil oil (*Ocimum tenuiflorum*) and clove oil.

15. The method of claim 1 wherein the mouthwash further consists essentially of (c) at least one mint oil selected from the group consisting of wintergreen oil and spearmint oil and (d) at least one anti-inflammatory oil selected from the group consisting of holy basil oil and clove oil.

16. The method of claim 1 wherein the mouthwash further consists essentially of (c) at least one mint oil selected from the group consisting of wintergreen oil and spearmint oil, (d) at least one oil selected from the group consisting of holy basil (*Ocimum tenuiflorum*) oil and clove oil and (e) xylitol at a concentration of at least 5%.

17. A method for reducing gingival inflammation by at least 25% as measured on the Löe-Silness gingival index a step of daily administration for at least 60 seconds of a toothpaste prior to the step of daily administration for at least 60 seconds of a mouthwash according to claim 16, wherein the toothpaste consists essentially of
  (a) Dead Sea salt at a concentration of from about 0.5% to about 3.0%.
  (b) Aloe vera leaf juice at a concentration of at least 40% wherein the toothpaste does not contain a bleaching agent and does not contain a fluoride source.

18. The method of claim 17 wherein the toothpaste further consists essentially of (c) xylitol at a concentration of at least 10% and (d) at least one mint oil selected from the group consisting of wintergreen oil at a concentration of up to 1% or spearmint oil at a concentration of up to 4%.

19. The method of claim 17 wherein the toothpaste further consists essentially of (c) xylitol at a concentration of at least 10% and (d) at least one anti-inflammatory oil selected from the group consisting of holy basil oil (*Ocimum tenuiflorum*) and clove oil.

* * * * *